United States Patent
Tschackert

(10) Patent No.: US 9,387,053 B2
(45) Date of Patent: Jul. 12, 2016

(54) DENTAL SPLINT MADE OF TWO PLASTICS WITH DIFFERENT DEGREES OF HARDNESS

(76) Inventor: Steffen G. Tschackert, Frankfurt am Main (DE)

( * ) Notice: Subject to any disclaimer, the term of this patent is extended or adjusted under 35 U.S.C. 154(b) by 332 days.

(21) Appl. No.: 13/817,696

(22) PCT Filed: Aug. 16, 2011

(86) PCT No.: PCT/EP2011/064100
§ 371 (c)(1),
(2), (4) Date: Feb. 19, 2013

(87) PCT Pub. No.: WO2012/022748
PCT Pub. Date: Feb. 23, 2012

(65) Prior Publication Data
US 2013/0146067 A1    Jun. 13, 2013

(30) Foreign Application Priority Data
Aug. 19, 2010   (DE) .......................... 10 2010 037 075

(51) Int. Cl.
*A61C 5/14*   (2006.01)
*A63B 71/08*  (2006.01)

(52) U.S. Cl.
CPC .................. *A61C 5/14* (2013.01); *A63B 71/085* (2013.01); *A63B 2071/086* (2013.01)

(58) Field of Classification Search
USPC .......................... 128/849, 859–856; 433/6–7
See application file for complete search history.

(56) References Cited

U.S. PATENT DOCUMENTS

| 4,370,129 A * | 1/1983 | Huge ....................... A61C 7/08 433/6 |
| 5,056,534 A * | 10/1991 | Wright ..................... A61F 5/566 128/848 |
| 6,935,857 B1 | 8/2005 | Farrell |
| 2003/0019497 A1 | 1/2003 | Farrell |

(Continued)

FOREIGN PATENT DOCUMENTS

| DE | 4020647 A1 | 1/1992 |
| DE | 69932083 T2 | 6/2007 |

(Continued)

OTHER PUBLICATIONS

International Search Report dated Jun. 12, 2011, as issued in corresponding International Patent Application No. PCT/EP2011/064100, filed Aug. 16, 2011 (with English Translation)—6 pgs.

(Continued)

*Primary Examiner* — Ophelia A Hawthorne
(74) *Attorney, Agent, or Firm* — Maier & Maier, PLLC

(57) ABSTRACT

The invention relates to a dental splint with a U-shaped base and wall-shaped reinforcements on the tongue and lip sides, said reinforcements forming channels, and to a method for the production of said dental splint. Said splint consists of different plastics of different degrees of hardness. The dental splint is thus flexible, offers a high degree of wearing comfort, and causes an increase in power and endurance in the wearer during athletic activities. An upper jaw dental splint can also be used as a mouth guard in contact sports with an additional reinforcement. Said dental splint for the upper jaw can be designed such that a free space is formed in the front teeth region after inserting the dental splint and clenching the teeth, whereby additional air for breathing can reach the oral cavity.

2 Claims, 4 Drawing Sheets

(56) References Cited

U.S. PATENT DOCUMENTS

Figure 1:
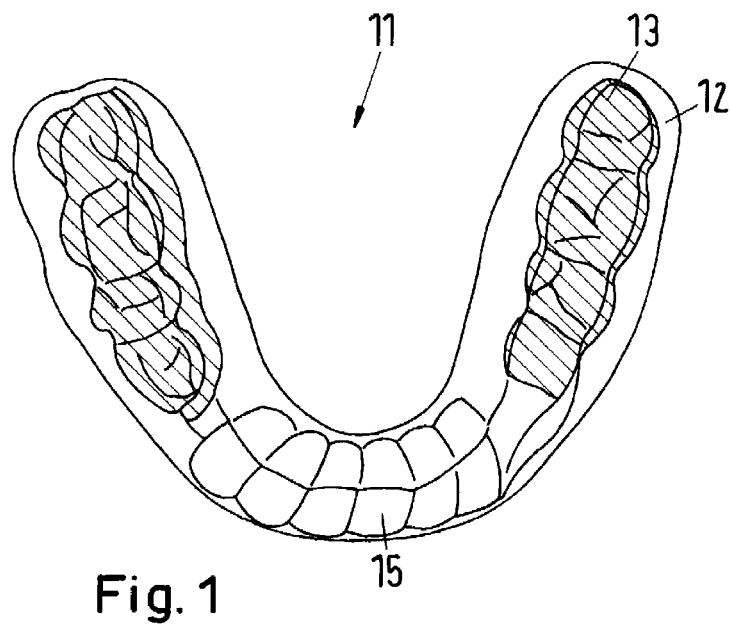

| | | |
|---|---|---|
| 2004/0103905 A1 | 6/2004 | Farrell |
| 2006/0008760 A1* | 1/2006 | Phan et al. ......................... 433/6 |
| 2006/0219250 A1 | 10/2006 | Farrell |
| 2007/0235039 A1* | 10/2007 | Gottsch ................ A63B 71/085 128/859 |
| 2008/0138766 A1 | 6/2008 | Jansheski |

FOREIGN PATENT DOCUMENTS

| | | |
|---|---|---|
| DE | 102008061325 A1 | 4/2010 |
| EP | 2 000 111 A1 | 12/2008 |
| WO | 2007128270 A2 | 11/2007 |
| WO | 2009155223 A1 | 12/2009 |

OTHER PUBLICATIONS

German Office Action dated Aug. 19, 2010, in connection with German Application No. 10 2010 037 075.4-43.

\* cited by examiner

DENTAL SPLINT MADE OF TWO PLASTICS WITH DIFFERENT DEGREES OF HARDNESS

RELATED APPLICATIONS

This is the U.S. national stage application which claims priority under 35 U.S.C. §371 to International Patent Application No. PCT/EP2011/064100 filed on Aug. 16, 2011, which claims priority to German Patent Application No 10 2010 037 075.4 filed on Aug. 19, 2010, the disclosures of which are incorporated by reference herein their entireties.

The present invention relates to a dental splint with a U-shaped base and channel-forming wall-shaped reinforcements on the tongue and lip sides.

Dental splints and mouth guards are commonly used for a variety of purposes, both in the medical field and in the sports sector.

Dental splints or braces in the form of removable or fixed devices are used in children and adults to correct misaligned teeth. Bite splints are made to stop tooth wear in the case of bruxism (teeth grinding). In addition, thin dental splints are used in teeth whitening.

In amateur and professional sports, mouth guards are primarily used for protective purposes and cover the teeth and parts of the jaw bone. In contact sports such as (American) football, boxing, basketball, or handball, it is easy to get shocks and blows to the face and jaw. Mouth guards are therefore intended to prevent or reduce injury to teeth and the jaw bone. Even in the case of stronger shocks, such a mouth guard can reduce the extent of injury to the head.

A purely protective mouth guard is for example described in the document U.S. Pat. No. 5,406,963 A. Such protective mouth guards are known in various embodiments.

The mouth guard of publication U.S. Pat. No. 5,293,880 A is used to prevent injury in the head area during athletic activities and can be attached to a helmet or similar headgear. The document CA 2700544 A1 describes a protective mouth guard, which is also provided with customizable color inserts. However, these mouth guards offer protection only against shocks to the head region.

The publication U.S. 2002144693 A1 describes a mouth guard with a protective function. A disadvantage of this mouth guard is that it is composed of different parts, which may cause hygienic problems during cleaning. Due to its massive construction, this mouth guard is suitable only for use in contact sports. In purely athletic sports, this compact mouth guard is cumbersome and annoying to the mouth.

The object of the present invention was to develop a dental splint which can be individually adapted to the wearer, ensures a comfortable fit, and also provides beneficial properties to improve performance in professional and amateur sports.

The object is achieved by a dental splint according to claim 1 and a process for the production thereof.

The dental splint according to the present invention is made up of a U-shaped base having channel-forming wall-shaped reinforcements on the tongue and lip sides. It is composed of at least two plastics with different degrees of hardness; the dental splint has a one-piece construction and can therefore be easily cleaned.

The plastic covering the molars has a lower degree of hardness than the plastic surrounding the front teeth. This combination of plastics having different hardnesses allows a high degree of wearer comfort with full functionality. Because of the flexibility of the dental splint according to the present invention it can be worn in purely athletic sports, and does not disturb the wearer.

The dental splint is made for either the upper or the lower jaw and is customized to the tooth shape and jaw position of the wearer.

In one embodiment of the present invention, the plastic used has a thickness of 1 mm-10 mm, preferably 2 mm-6 mm, more preferably from 2.5 mm-3.5 mm.

In a preferred specific embodiment, the plastic used for reinforcement of the dental splint, which is applied in an additional layer on the splint in the region of the complete dentition, has a thickness of 0.1 mm-5 mm, preferably 0.5 mm-3 mm, particularly preferably 0.8 mm-1.5 mm.

The dental splint according to the present invention is used to improve the performance of a wearer during sport activity. The dental splint according to the present invention fixes the ideal, relaxed jaw position (rest position). Thus, the dental splint increases the wearer's strength, body mobility, speed, and body equilibrium. It is suitable for use in individual sports, such as swimming, track and field, or golf, as well as team sports. In contact sports such as football, boxing, ice hockey or handball, it is advantageous to use the dental splint according to the present invention for the upper jaw. This splint is additionally reinforced and thus can be used simultaneously as a mouth guard.

Furthermore, it is preferred that after inserting the dental splint and biting with the teeth, a free space arises in the front-teeth region so that additional air for breathing can pass into the oral cavity. In particular, it is provided that this free space is produced in the front-teeth region in the dental splint for the upper jaw, but the dental splint for the lower jaw can also be formed such that a free space is created in the front-teeth region. The front-teeth region is here meant to refer to the front teeth 13, 12, 11 and 21, 22, 23.

When a wearer of the dental splint for the upper jaw closes his jaws, the teeth of the lower jaw come into contact with the splint on the upper jaw teeth. This leads to a fixed bite contact and an almost airtight seal between the teeth of the lower jaw and the dental splint on the upper jaw. This problem exists in particular in the dental splint for the upper jaw if it is also used, with an additional reinforcement, as a mouth guard.

Since in this bite position of the jaw breathing through the mouth becomes more difficult, the dental splint can be designed such that in the area of the front teeth (13, 12, 11, 21, 22, 23), a free gap arises in the incisal area. Here, a biting contact of the teeth of the lower jaw with the dental splint on the upper jaw exists only in the area of the teeth 16, 15, 14 and 26, 25, 24 (premolars and molars). The front teeth of the lower jaw, however, have no contact with the dental splint. This results in a narrower free space in the region of the front teeth (13, 12, 11, 21, 22, 23), so that additional breathing air can pass into the mouth of the wearer.

The above object is also achieved by a process for producing a dental splint, including at least the following steps:

For the production of the dental splint, first the optimal jaw position of the wearer for whom the dental splint is to be produced is determined. Subsequently, a positive impression of the dentition is formed (plaster cast), and the dental impression is molded with a plastic material having a high degree of hardness, the plastic in the area of the molars being subsequently removed again and the dental impression being molded again with a plastic having a lower degree of hardness. The two impressions are applied to the positive impression of the dentition and are then fixed by a further plastic layer. Subsequently, the molding of the dental impression is carried out by mechanical pressure on the preheated plastic having low hardness.

Further advantages and details for a better understanding of the present invention are shown in the description of the Figures presented below on the basis of an exemplary embodiment.

Figure 2:
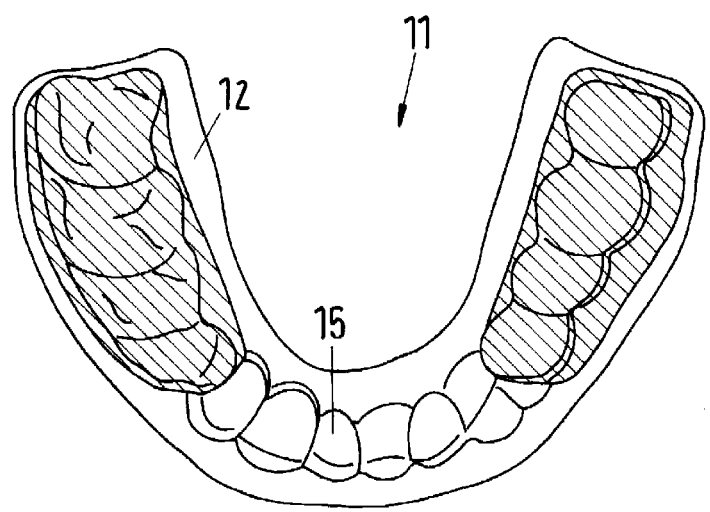
Figure 3:
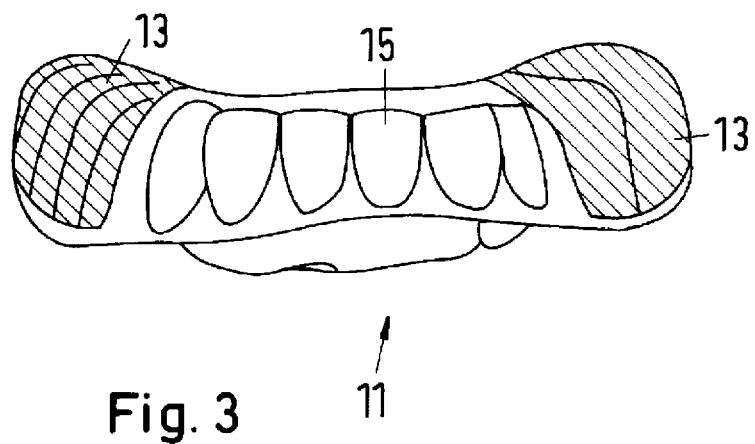
Figure 4:
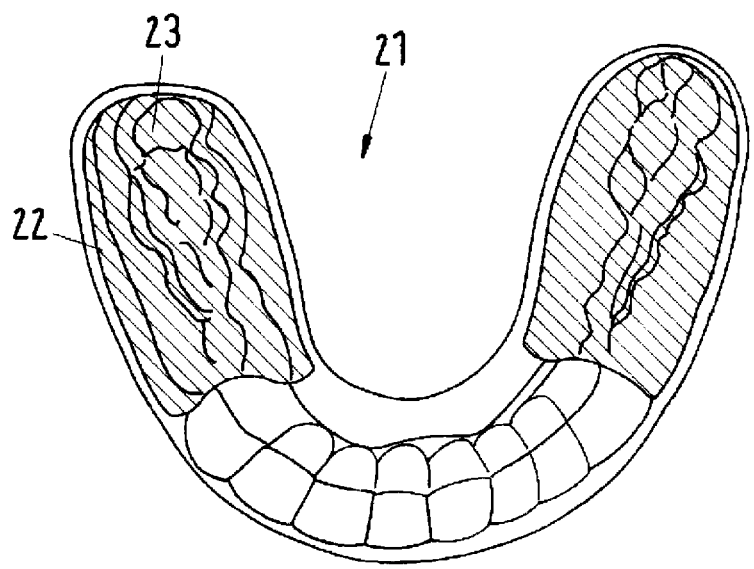
Figure 5:
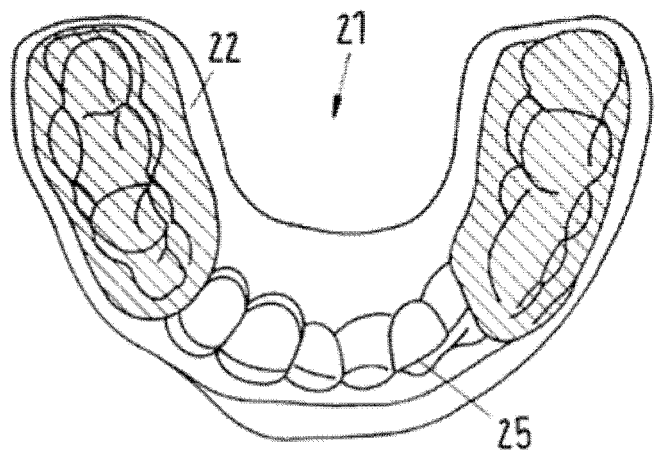
Figure 6:
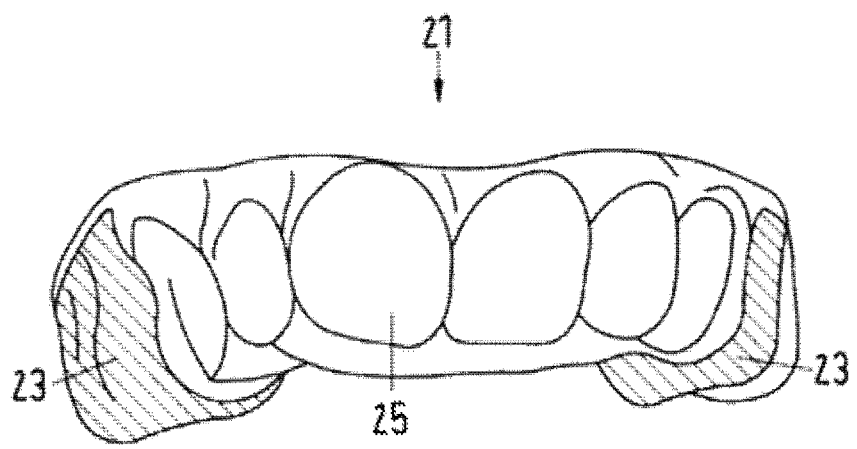
Figure 7:
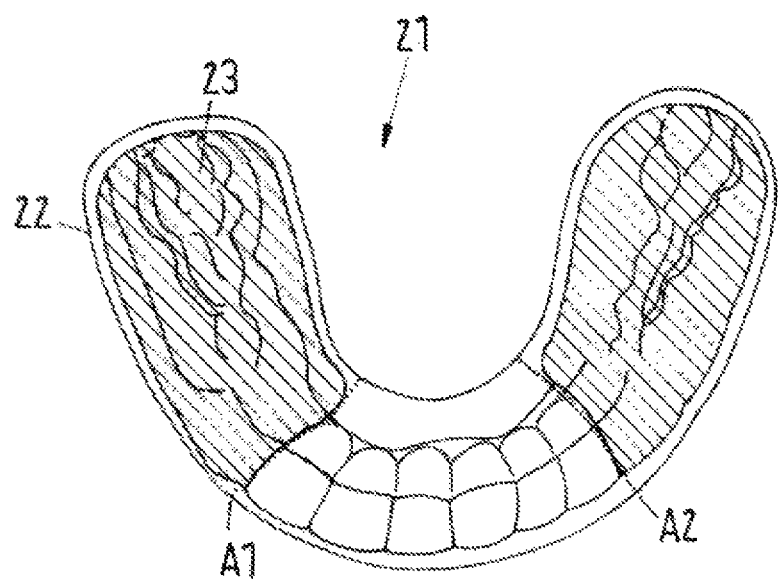

FIG. 1 shows the top view of the outer surface of a dental splint for the lower jaw, FIG. 2 shows the top view of the inner surface of a dental splint for the lower jaw, FIG. 3 shows the front view of the splint in the region of the lower jaw front teeth, FIG. 4 shows the top view of the outer surface of a dental splint for the upper jaw, FIG. 5 shows the top view of the inner surface of a dental splint for the upper jaw, FIG. 6 shows the front view of the splint in the region of the upper jaw front teeth, FIG. 7 shows the top view of the outer surface of a dental splint for the upper jaw, which forms an additional free space in the front-teeth region of the wearer.

FIGS. 1-3 show an example of the dental splint according to the present invention for the lower jaw, while FIGS. 4-6 show the dental splint according to the present invention for the upper jaw. The dental splint 11 and 21 according to the present invention is made up of two different plastic materials having different degrees of hardness. In the area of the molars, a plastic with a lower Shore hardness 13 and 23 and a thickness of 3 mm is used for the dental splint. In the area of the front teeth, however, a plastic with a higher Shore hardness of 15 and 25, preferably having a thickness of 0.5 to 3 mm, is used for the dental splint.

In the process according to the present invention, first the plastic having the high Shore hardness of 15 and 25 is applied to the dentition model, and then the area of the molars is removed. In a second step, the plastic having the lower degree of hardness 13 and 23 is shaped onto the entire dentition, and then the area of the front teeth is removed. Both areas are then applied to the positive impression and are fixed by a further layer of plastic 12, 22. In this way, the plastic having lower hardness 13 and 23 comes to lie adjacent the plastic having the higher hardness. The position of the jaws relative to one another is fixed by mechanical force applied to the heated plastic having lower degree of hardness 13 and 23.

The dental splint for the upper jaw 21 has in addition a further plastic layer 25 with a higher Shore hardness and a thickness of 1 mm as a reinforcement, thus protecting the wearer against impacts in the jaw area.

FIG. 7 shows, as in FIGS. 4 and 6, a dental splint for the upper jaw 21 which is equipped with a plastic having a lower hardness 23 in the region of the molars and is equipped with a plastic material having a higher Shore hardness in the area of the front teeth (teeth 13, 12, 11, 21, 22, 23). The two areas of the front teeth and the molars, having the differing plastic hardnesses, are connected to one another by a further layer of plastic with a softer hardness 22. In this dental splint for the upper jaw as well, another layer of plastic with a higher Shore hardness and a thickness of 1 mm can then be applied as a reinforcement, thus protecting the wearer against impacts in the jaw area.

This embodiment of the dental splint according to the present invention for the upper jaw 21 forms in the mouth of the wearer an additional free space in the region of the front teeth (A1-A2), which can act as a breathing opening.

Because in particular when wearing the dental splint for the upper jaw, which can also act as a mouth guard, the clenching of the jaw causes a firm bite contact throughout the entire splint area, making breathing through the mouth more difficult, the dental splint is therefore provided with an additional breathing opening.

This opening is designed as a free space in the front-teeth region of the dental splint and results when side teeth 16, 15, 14 and 26, 25, 24 (premolars and molars) bite down. Here the teeth of the lower jaw only have contact with the dental splint in the upper jaw in the area of the teeth 16, 15, 14 and 26, 25, 24. In contrast, the front teeth of the lower jaw have no contact with the dental splint. This results in a narrow intermediate gap in the area of the front teeth (A1-A2) between the splint of the upper jaw and the incisal region of the front teeth of the lower jaw. Through this narrow space, additional breathing air is allowed into the mouth of the wearer.

Further advantages and details for a better understanding of the process for producing the dental splint according to the present invention can be learned from the following description, with reference to an exemplary embodiment.

First, an electromyogram (EMG) is used to carry out a muscle function analysis in the head of the wearer. In the tensioned state, bite positions and the relaxed position of the jaw can be determined. After relaxation, caused if necessary using a TENS device, the positioning of the jaw for the desired splint position of the user is carried out. Each individual jaw position should be found in which the masticatory muscles are in their relaxed state. The positioning of the jaw is carried out using a muscle analysis device, the K7 system of the company Myotronics.

Three to four different jaw positions are determined—the ideal position and positions just before and just behind it. In the optimal jaw position, there is a narrow gap between the teeth of the upper jaw and of the lower jaw; this is called the rest position. This position is different from person to person and therefore must be determined individually. A bite registration is taken of each of these positions. From this bite registration, a model of each jaw position is produced. The dental splint according to the present invention then fills this gap and positions the jaw in its optimal position.

The material for the dental splint is preferably a copolymer suitable for use in the dental field. Here, a suitable copolymer of the same kind, but with different Shore hardnesses, can be used, as can different copolymers with different Shore hardnesses. Particularly preferably, ethylene vinyl acetate (EVA) is used. In a preferred embodiment, Bioplast of the company Scheu, in the form of a thermoforming sheet, is used as EVA.

First, the plastic having a high Shore hardness is used. The corresponding thermoforming sheet has a thickness of 0.5 to 3 mm and is pulled over the dentition model, and the plastic in the area of the molars is subsequently removed. Subsequently the dental impression is molded again using a thermoforming sheet with a low degree of hardness, also having a thickness of 3 mm, and the plastic is removed in the area of the front teeth; the plastic has a lower Shore hardness than the plastic from the previous step. Subsequently, both impressions are applied onto the positive cast of the teeth and are then fixed by a further thermoforming sheet having low hardness. The dental impression of the opposite jaw in the area of the molars is molded by subsequent heating and mechanical application of force. This process thus allows the production of a flexible dental splint with high wearer comfort that nonetheless allows a strong guiding of the dentition. The process for producing the dental splint according to the present invention for the lower jaw and for the upper jaw is identical up to this step.

If a dental splint for the upper jaw is produced for the wearer that provides an additional protective function in the front teeth region, then a further plastic layer having a thickness of 1 to 5 mm is applied over the dental splint in the front teeth region.

The present invention in all variant embodiments is not limited to a specific polymeric color combination of the various copolymers. Moreover, it is possible to provide the dental splint according to the present invention with logos, for example of the manufacturer or of a team.

REFERENCE CHARACTERS

11. Dental splint for the lower jaw
12. Plastic having softer hardness
13. Plastic having lower hardness in the area of the molars
15. Plastic having higher hardness in the area of the front teeth
21. Dental splint for the upper jaw
22. Plastic having softer hardness
23. Plastic having lower hardness in the area of the molars
25. Plastic having higher hardness in the area of the front teeth
A1-A2. Area of the breathing opening

The invention claimed is:

1. A process for producing a dental splint comprising:
Determining an optimal jaw position, a rest position, where a narrow gap between teeth of an upper jaw and of a lower jaw exists,
Taking a bite registration of the optimal jaw position,
Producing a model of each jaw position from the bite registration,
Molding a dental impression of each jaw position with a plastic of a high degree of hardness using a positive cast of a dentition,
Removing the plastic in a region of one or more molars and removing the plastic molding,
Re-molding the dental impression with a plastic of a lower degree of hardness,
Removing the plastic in a region of one or more front teeth,
Applying the two plastic moldings on the positive cast,
Applying a plastic layer for fixing the two moldings,
Heating the plastic molding, and
Molding the dental impression of an opposite jaw in the region of the molars
wherein the dental splint produced is for the upper jaw or the lower jaw with a U-shaped base and channel-forming wall-shaped reinforcements on tongue and lip sides, wherein the plastic which covers the molars has a lower degree of hardness than the plastic which is adapted to contact the one or more front teeth, and the dental splint puts the jaw of a wearer to an optimal position by filling the narrow gap between the teeth of the upper jaw and of the lower jaw that exists in an optimal jaw position, and after inserting the dental splint for the upper jaw and biting down, the teeth of the lower jaw are only adapted to contact with the dental splint for the upper jaw in a region of one or more premolars and the molars so that a free space in the front teeth region is created through which additional air for breathing can enter an oral cavity.

2. Process for producing a dental splint for the upper jaw with additional reinforcement of the one or more front teeth according to claim 1, wherein a further plastic layer having a thickness of 1-5 mm is applied over the dental splint in the front teeth region.

* * * * *